United States Patent
Van Atta et al.

(10) Patent No.: US 6,991,333 B2
(45) Date of Patent: Jan. 31, 2006

(54) EYEWEAR WITH REPLACEABLE LENS

(75) Inventors: Dylan S. Van Atta, Portland, OR (US); Robert Barnette, Portland, OR (US); Robert M. Bruce, Portland, OR (US); Mark J. Eastwood, Kentfield, CA (US)

(73) Assignee: Nike, Inc., Beaverton, OR (US)

( * ) Notice: Subject to any disclaimer, the term of this patent is extended or adjusted under 35 U.S.C. 154(b) by 46 days.

(21) Appl. No.: 10/777,480

(22) Filed: Feb. 12, 2004

(65) Prior Publication Data

US 2005/0179856 A1 Aug. 18, 2005

(51) Int. Cl.
G02C 11/08 (2006.01)

(52) U.S. Cl. .......................... 351/62; 351/103; 351/106; 351/136

(58) Field of Classification Search ............... 351/41, 351/44, 62, 103–109, 136–137; 2/435–437
See application file for complete search history.

(56) References Cited

U.S. PATENT DOCUMENTS

| | | | |
|---|---|---|---|
| 2,362,725 A | 11/1944 | Slotsky | 351/106 |
| 2,397,243 A | 3/1946 | Cooper, Jr. | 2/443 |
| 2,444,498 A | 7/1948 | Cochran | 351/106 |
| D150,924 S | 9/1948 | Bright | D16/315 |
| 2,534,655 A | 12/1950 | Baratelli | 2/431 |
| 2,563,125 A | 8/1951 | Malcolm, Jr. | 2/14 |
| 2,571,704 A | 10/1951 | Gilden | 351/106 |
| 2,607,919 A | 8/1952 | Stegeman | 2/443 |
| 2,770,806 A | 11/1956 | Moeller | 2/12 |
| 2,825,267 A | 3/1958 | Gagnon | 351/52 |
| D182,459 S | 4/1958 | Eisler | D16/316 |
| 3,066,573 A | 12/1962 | Moeller | 351/60 |
| 3,233,249 A | 2/1966 | Baratelli et al. | 2/443 |
| 3,517,393 A | 6/1970 | Beauchef | 2/436 |
| 3,756,704 A | 9/1973 | Marks | 351/106 |
| 3,838,914 A | 10/1974 | Fernandez | 351/106 |
| 4,317,240 A | 3/1982 | Angerman et al. | 2/436 |
| 4,674,851 A | 6/1987 | Jannard | 351/47 |
| D293,450 S | 12/1987 | Jannard | D16/102 |
| 4,730,915 A | 3/1988 | Jannard | 351/47 |
| 4,824,233 A | 4/1989 | Jannard | 351/47 |
| 4,951,322 A | 8/1990 | Lin | 2/439 |
| D324,394 S | 3/1992 | Jannard | D16/103 |
| 5,249,001 A | 9/1993 | Jannard | 351/123 |
| 5,387,949 A | 2/1995 | Tackles | 351/121 |
| 5,467,148 A | 11/1995 | Conway | 351/85 |
| 5,555,037 A | 9/1996 | Canavan | 351/118 |
| 5,576,775 A | 11/1996 | Bolle | 351/62 |
| 5,841,505 A | 11/1998 | Bolle' | 351/62 |
| 5,969,787 A * | 10/1999 | Hall et al. | 351/62 |
| 6,119,681 A1 | 3/2001 | Canavan | 351/106 |
| 6,367,927 B2 | 4/2002 | Yang | 351/103 |
| 6,517,202 B2 | 2/2003 | Huang | 351/103 |
| 6,783,235 B1 * | 8/2004 | Lin | 351/62 |

FOREIGN PATENT DOCUMENTS

| | | |
|---|---|---|
| IT | 01311533 | 7/1999 |
| WO | WO 00/36453 | 6/2000 |

* cited by examiner

Primary Examiner—Huy Mai
(74) Attorney, Agent, or Firm—Banner & Witcoff, Ltd.

(57) ABSTRACT

Eyewear with a replacement lens include an elongate center member, a pair of temple arms, and a pair of connecting members. Each connecting member is secured to one of the temple arms and to the center member, and has a slot formed in a surface thereof. A lens is received in the slots of the connecting members, with a rear surface of the lens along an upper edge of the lens being spaced from the center member so as to form a gap therebetween. A nosepiece may be secured to a lower edge of the lens.

55 Claims, 4 Drawing Sheets

EYEWEAR WITH REPLACEABLE LENS

FIELD OF THE INVENTION

This invention relates generally to eyewear, and, in particular, to eyewear with a replaceable lens having improved ventilation.

BACKGROUND OF THE INVENTION

Eyewear with replaceable lenses is well known in the art. In certain applications, eyewear has multiple replacement lenses to accommodate different lighting conditions. Eyewear may incorporate a wraparound lens, commonly referred to as a shield lens. Eyewear with a wraparound lens is often used by individuals when they are engaged in athletic activities, such as biking, skiing, and running. A problem common to such eyewear is that they can fog up due to the heat and perspiration generated by the user during such athletic activities.

U.S. Pat. No. 5,576,775 to Bolle discloses eyewear with a frame supporting a curved lens along an upper edge thereof. Each one of a pair of temple arms is attached by a hinge to an outer side of the frame. Bosses extend downwardly from the frame, and have slots in their lower surfaces that receive the lens. Gaps are formed between an upper edge of the lens and a lower edge of the frame, between each of the bosses, in order to provide ventilation for the eyewear.

U.S. Pat. No. 5,841,505 to Bolle discloses sunglasses having an elongate curved frame. A curved wraparound lens is secured to a central portion of the frame. The lens of Bolle is spaced from the frame along left and right portions of the lens, creating gaps between the lens and the frame. The lens is secured to the frame by a plurality of screws. Replacement of the lens of Bolle requires a screwdriver and a plurality of small screws.

It is an object of the present invention to provide eyewear with a replaceable lens that reduce or overcome some or all of the difficulties inherent in prior known devices. Particular objects and advantages of the invention will be apparent to those skilled in the art, that is, those who are knowledgeable or experienced in this field of technology, in view of the following disclosure of the invention and detailed description of certain preferred embodiments.

SUMMARY

The principles of the invention may be used to advantage to provide eyewear with a construction that facilitates easy replacement of the lens and improved ventilation.

In accordance with a first aspect, eyewear with a replaceable lens includes an elongate center member, a pair of temple arms, and a pair of connecting members. Each connecting member is secured to one of the temple arms and to the center member, and has a slot formed in a surface thereof. A lens is received in the slots of the connecting members, with a rear surface of the lens along an upper edge of the lens being spaced forwardly from the center member so as to form a gap therebetween.

In accordance with another aspect, eyewear with a replaceable lens includes an elongate center member, a pair of temple arms, and a pair of connecting members. Each connecting member is secured to one of the temple arms and to the center member, and has a slot formed in a surface thereof. A lens has an upper edge, a first tab at a first end of the upper edge, and a second tab at an opposed second end of the upper edge. The tabs of the lens are received in the slots of the connecting members such that a gap is formed between an outward surface of the center member and a rear surface of the lens along the upper edge of the lens.

In accordance with a further aspect, eyewear with a replaceable lens includes an elongate center member, a pair of temple arms, and a pair of connecting members. Each connecting member is secured to one of the temple arms and to the center member, and has a slot formed in a lower surface thereof. A lens has a lower edge and an upper edge. A recess is formed in the lower edge of the lens. A first tab is located at a first end of the upper edge, and a second tab is located at an opposed second end of the upper edge. The first and second tabs are received in the slots of the connecting members such that a gap is formed between an outward surface of the center member and a rear surface of the lens along the upper edge of the lens between the connecting members. Each arm of an inverted V-shaped nosepiece includes a projection and a planar surface. Each projection engages a notch in the recess and each planar surface abuts against a rear surface of the lens such that the projections and planar surfaces cooperate to secure the nosepiece to the lens.

In accordance with yet a further aspect, eyewear with a replaceable lens includes an elongate center member, a pair of temple arms, and a pair of connecting members. Each connecting member is secured to one of the temple arms and to the center member, and has a slot formed in a surface thereof. A lens has an upper edge, with a first end of the upper edge being received in the slot formed in one of the connecting members. An opposed second end of the upper edge is received in the slot formed in the other of the connecting members. The upper edge of the lens between its first and second ends is spaced from the center member so as to form a continuous gap therebetween.

Substantial advantage is achieved by providing such eyewear with a replaceable lens in accordance with preferred embodiments of the present invention. In particular, eyewear with a replaceable lens in accordance with preferred embodiments of the present invention provides increased ventilation, reducing the chance of fogging of the lens. This is highly advantageous since the user does not need to cease the activity they are involved in to clear their lenses, thereby enhancing visibility and safety.

These and additional features and advantages of the invention disclosed here will be further understood from the following detailed disclosure of certain preferred embodiments.

Figure 1:
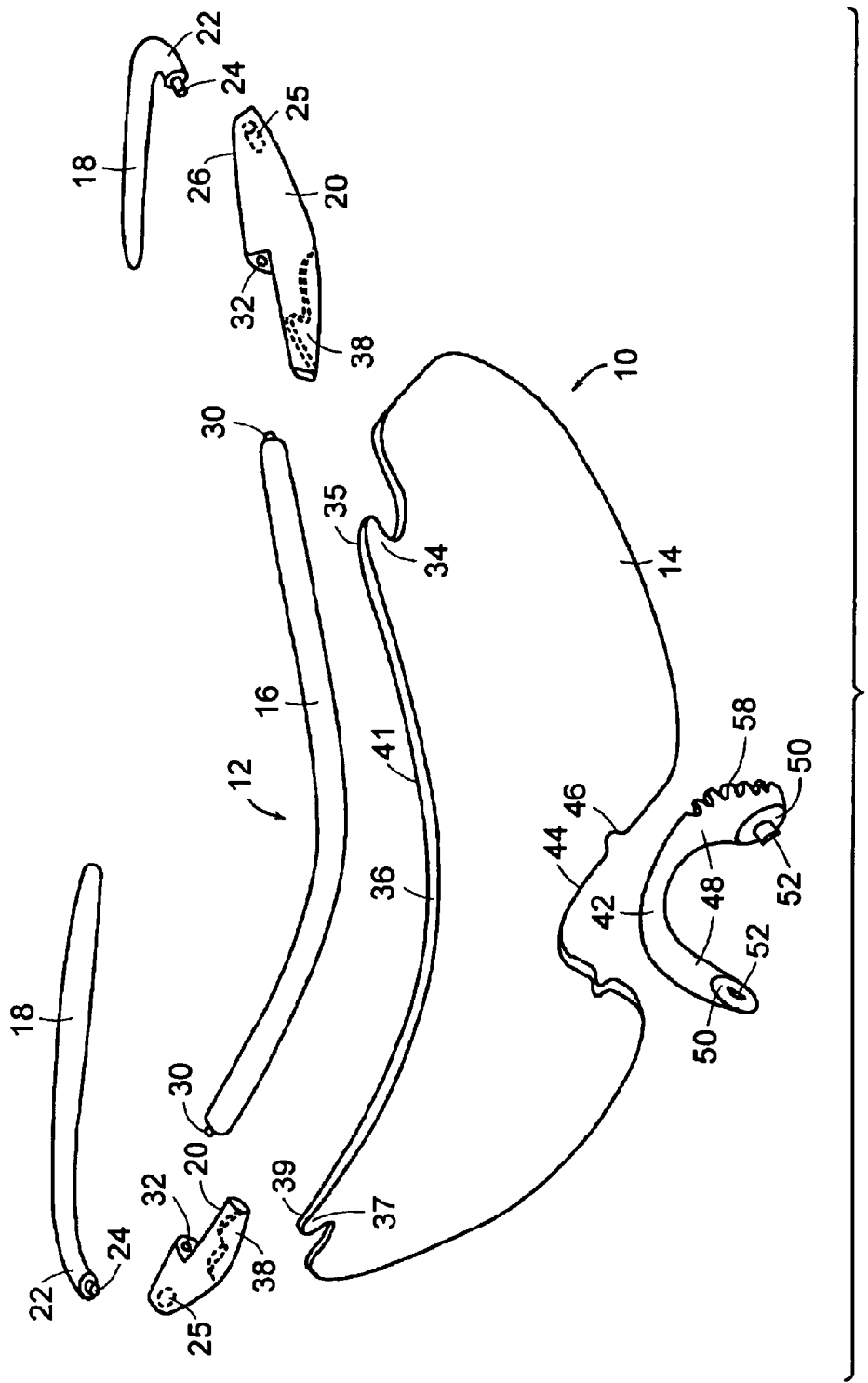
FIG. 1 is an exploded view of a preferred embodiment of eyewear with a replaceable lens, in an unassembled condition, in accordance with the present invention.

The figures referred to above are not drawn necessarily to scale and should be understood to present a representation of the invention, illustrative of the principles involved. Some features of the eyewear with a replaceable lens depicted in the drawings have been enlarged or distorted relative to others to facilitate explanation and understanding. The same reference numbers are used in the drawings for similar or identical components and features shown in various alternative embodiments. Eyewear with a replaceable lens as disclosed herein would have configurations and components determined, in part, by the intended application and environment in which it is used.

DETAILED DESCRIPTION OF CERTAIN PREFERRED EMBODIMENTS

Figure 2:
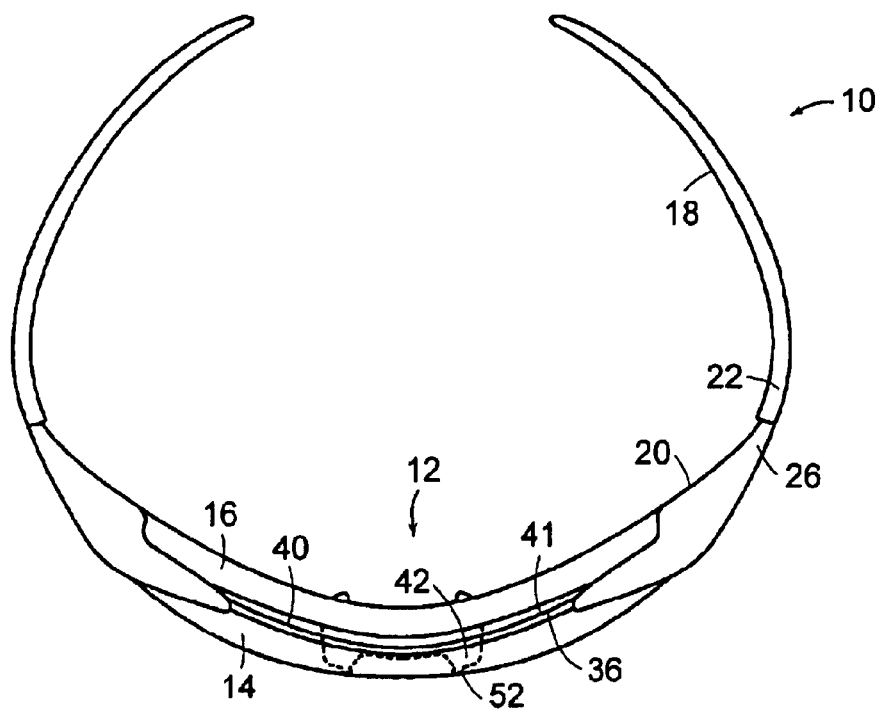
FIG. 2 is a top plan view of the eyewear of FIG. 1, in an assembled condition.
Figure 3:
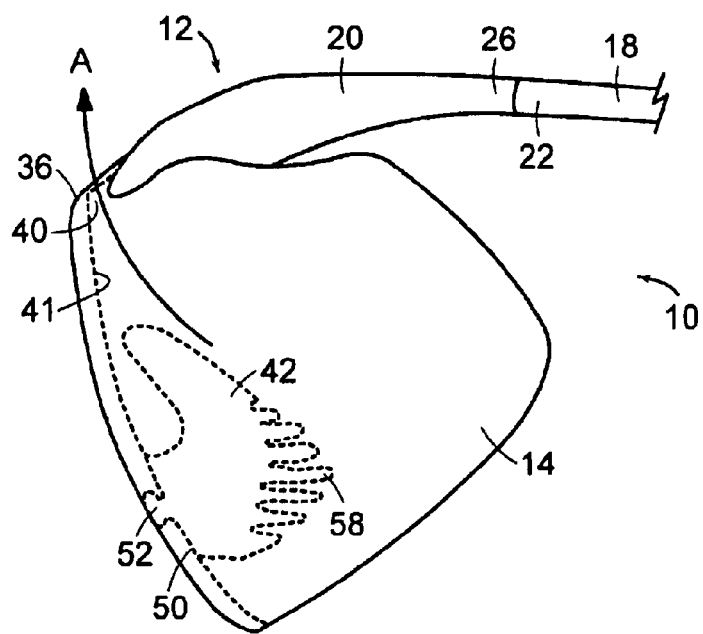
FIG. 3 is a side elevation view of the eyewear of FIG. 1, in an assembled condition.

The present invention may be embodied in various forms. A preferred embodiment of eyewear 10 is shown in FIGS. 1–3. In certain preferred embodiments, eyewear 10 is sunglasses. In particular, the embodiments depicted herein illustrate use of the present invention with performance sunglasses, typically used by bicycle riders and runners. However, it is to be appreciated that eyewear 10 is meant to include all types of glasses, including, for example, prescription glasses and safety glasses with clear lenses.

Certain directional terms used herein refer to directions with respect to the wearer of eyewear 10. Thus, the terms outward, outwardly, forward, and forwardly, as used herein, refer to a surface facing away from, or a direction extending away from, the face of a wearer of eyewear 10. The terms inward, inwardly, rear, and rearwardly refer to a surface facing toward, or a direction extending toward, the face of a wearer of eyewear 10.

Eyewear 10 includes a frame 12 and a lens 14 secured to frame 12. Frame 12 includes an elongate center member 16. In a preferred embodiment, center member 16 is curved rearwardly in order to match the contour of the forehead of the wearer of eyewear 10. Center member 16 may be formed of a rigid material, for example, a fiber-reinforced material such as a carbon fiber composite, providing a rigid structure and support for lens 14. In other embodiments, center member 16 may be formed of plastic, or a rubber coated core material, such as metal or plastic.

Other suitable materials for center member 16 will become readily apparent to those skilled in the art, given the benefit of this disclosure. As illustrated here, center member 16 is substantially cylindrical, however, it is to be appreciated that center member 16 may have any cross-sectional profile.

Each of a pair of temple arms 18 is connected to center member 16 by way of a connecting member 20. A first end 22 of each temple arm 18 includes a projection 24 that is received by a mating recess 25 in a first end 26 of a connecting member 20. Projections 24 may be received in snap-fit fashion by recesses 25 in connecting member 20. Additionally, projections 24 may be secured within recesses 25 by an adhesive to further secure temple arms 18 to connecting members 20. In the illustrated embodiment, projections 24 and recesses 25 are substantially cylindrical, however, other shapes for projections 24 and recesses 25 are considered to be within the scope of the present invention.

It is to be appreciated that in certain preferred embodiments, a projection may alternatively be formed on first end 26 of each connecting member 20, with a corresponding recess formed in first end 22 of each temple arm 18. Other means of securing temple arms 18 to connecting members 20 will become readily apparent to those skilled in the art, given the benefit of this disclosure.

Temple arms 18 and connecting members 20 may be formed of any suitable material, including, for example, plastic, or a rubber coated core material, such as metal or plastic. In certain preferred embodiments, temple arms 18 and connecting members 20 are formed of a flexible, resilient material, such as beta titanium. In other embodiments, temple arms 18 and connecting members 20 may be formed of a rigid material, such as a fiber-reinforced material, e.g., a carbon fiber composite. Other suitable materials for temple arms 18 and connecting members 20 will become readily apparent to those skilled in the art, given the benefit of this disclosure.

It is to be appreciated that in certain preferred embodiments, temple arms 18 and connecting members 20 may be formed of unitary, that is, one piece, construction. In other embodiments, connecting members 20 and center member 16 may be of unitary construction. In still other embodiments, temple arms 18, connecting members 20 and center member 16 may be of unitary construction.

Each end of center member 16 is secured to a connecting member 20. In the illustrated embodiment, a projection 30 is formed on each end of center member 16, with each projection 30 being received in a mating recess 32 formed in a central portion of a connecting member 20.

Projections 30 may be received in snap-fit fashion by recesses 32 in connecting member 20. Additionally, projections 30 may be secured within recesses 32 by an adhesive to further secure center member 16 to connecting members 20. In the illustrated embodiment, projections 30 and recesses 32 are substantially cylindrical, however, other shapes for projections 30 and recesses 32 are considered to be within the scope of the present invention. It is to be appreciated that in certain preferred embodiments, a projection may alternatively be formed on each connecting member 20, with a corresponding recess formed in the ends of center member 16. Other means of securing center member 16 to connecting members 20 will become readily apparent to those skilled in the art, given the benefit of this disclosure.

Figure 4:
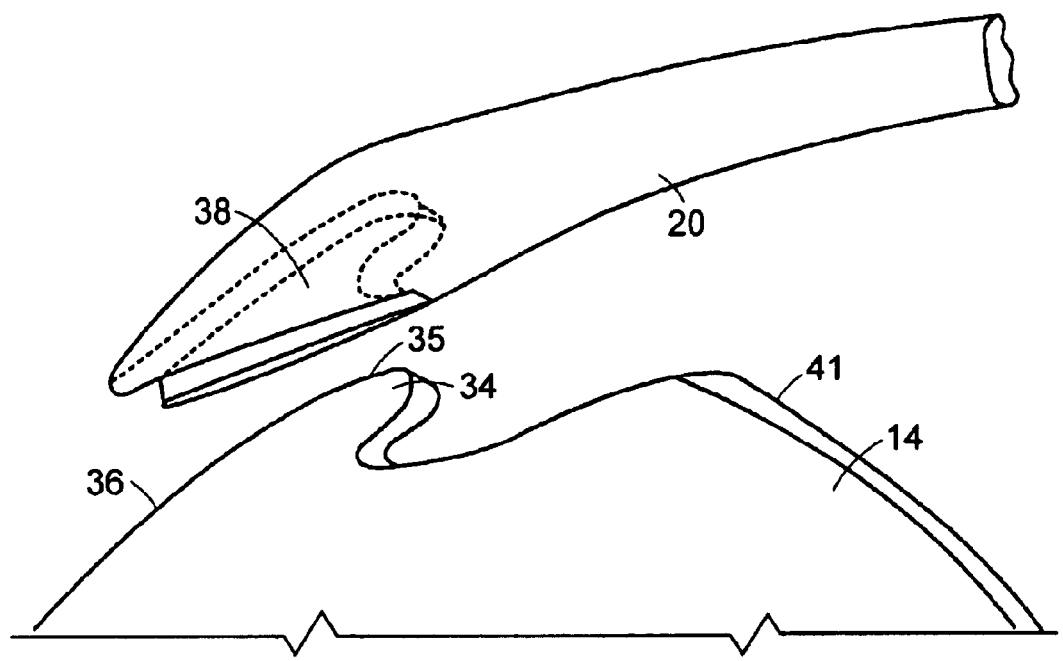
FIG. 4 is a side elevation view of a portion of the lens and connecting member of the eyewear of FIG. 1, shown prior to their engagement.

Lens 14 is secured to frame 12 by way of connecting members 20. A first tab 34 is formed at a first end 35 of an upper edge 36 of lens 14, and a second tab 37 is formed at an opposed second end 39 of lens 14. Each connecting member 20 has a groove 38, seen more clearly in FIG. 4, formed in a lower surface thereof. In the illustrated embodiment, grooves 38 are mirror images of tabs 34, 37 such that each tab 34, 37 mates in interlocking fashion with a corresponding groove 38. Lens 14 can be easily pressed into engagement with connecting members 20 by pushing tabs 34, 37 into grooves 38, and pulled from such engagement by pulling tabs 34, 37 out of grooves 38, thereby allowing a user to very quickly and easily replace lens 14 with an alternative or replacement lens.

As can be seen in FIGS. 2–3, lens 14 is secured to connecting members 20 such that an upper edge 36 of lens 14 is spaced from center member 16 by a continuous gap 40 extending along the length of upper edge 36 between first and second ends, 35, 39, where lens 14 is secured to connecting members 20. Gap 40 provides ventilation for eyewear 10 between lens 14 and center member 16, reducing the chance of fogging of lens 14. This is highly advantageous, as preferred embodiments of the present invention are often used by users during athletic activities, such as biking and running. Not only can fogging of the lens be annoying during athletic activities, it can potentially be dangerous such as, for example, when a bicycle rider is racing and visibility can be critical.

In certain preferred embodiments, a rear surface 41 of lens 14 along upper edge 36 is spaced forwardly from center member 16 by gap 40 extending along the length of upper edge 36 between connecting members 20. Gap 40 allows air, and especially heated air, to pass freely upwardly in the direction of Arrow A, as seen in FIG. 3. By constructing eyewear 10 such that gap 40 is positioned between an outward side of center member 16 and rear surface 41 of lens 14, a clear unobstructed path upwardly past lens 14 is provided. By providing a clear path for heated air to flow upwardly past lens 14, the tendency of lens 14 to fog is further reduced.

Figure 5:
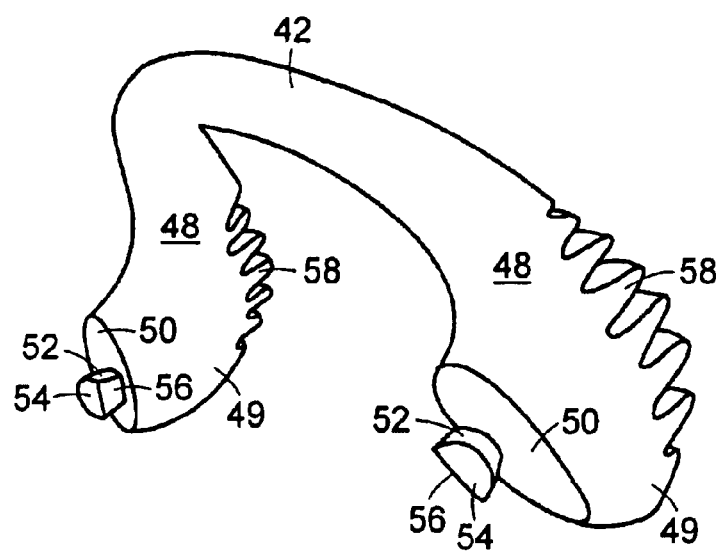
FIG. 5 is a perspective view of the nosepiece of the eyewear of FIG. 1.

In a preferred embodiment, a nosepiece 42 is secured to a central lower portion of lens 14. In the embodiment illustrated in FIGS. 1–3, an inverted V-shaped recess 44 is formed in the central lower portion of lens 14. A notch 46 is formed in each side of recess 44, and nosepiece 42 is secured to lens 14 by way of notches 46. As seen more clearly in FIG. 5, nosepiece 42 is an inverted V-shaped member having a pair of arms 48. The end 49 of each arm 48 turns forwardly and terminates in a forwardly facing planar surface 50. A projection 52 extends from each planar surface 50. In preferred embodiments, projection 52 is a frustoconical member having a base 54 spaced from and substantially parallel to planar surface 50, with a portion of planar surface 50 forming a top surface of frustoconical projection 52. Each projection 52 includes a planar surface 56 that extends from base 54 to planar surface 50, and is substantially perpendicular to base 54.

When nosepiece 42 is secured to lens 14, as seen in FIG. 3, each surface 50 abuts a rear surface of lens 14 adjacent recess 44 and each projection 52 is received by a corresponding notch 46, thereby capturing lens 14 and securing nosepiece 42 to lens 14. Planar surfaces 56 are substantially flush with the edge of lens 14 along recess 44. To remove nosepiece 42, the user grasps arms 48 and squeezes them together, thereby releasing projections 52 from their engagement with notches 46.

In a preferred embodiment, a plurality of rearwardly extending fins 58 is formed on a rear surface of each arm 48. Fins 58 rest on the bridge of the user's nose when eyewear 10 is worn by the user, and provide a positive gripping surface for nosepiece 42, reducing the chance of eyewear 10 slipping off the user's nose. Fins 58 also provide additional ventilation. Nosepiece 42 may be formed of rubber, which serves to provide good grip, plastic, or any other suitable material.

Figure 6:
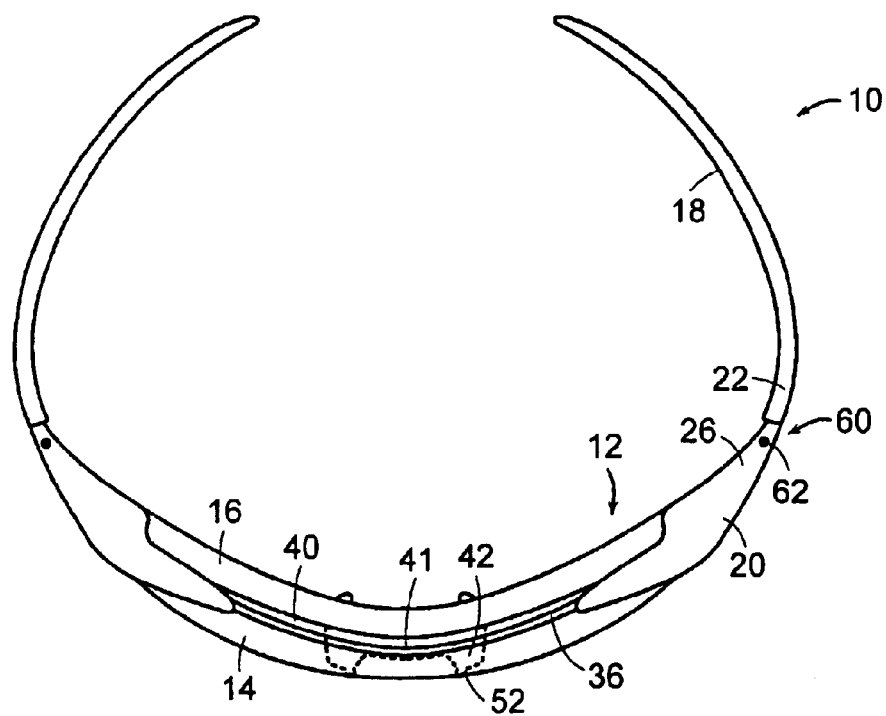
FIG. 6 is a top plan view of an alternative embodiment of the eyewear of the present invention.

Another preferred embodiment is shown in FIG. 6, in which temple arms 18 are pivotally secured to connecting member 20 by way of a hinge 60. In the illustrated embodiment, each hinge 60 includes a pin 62 extending through apertures (not shown) formed in temple arms 18 and connecting members 20.

Figure 7:
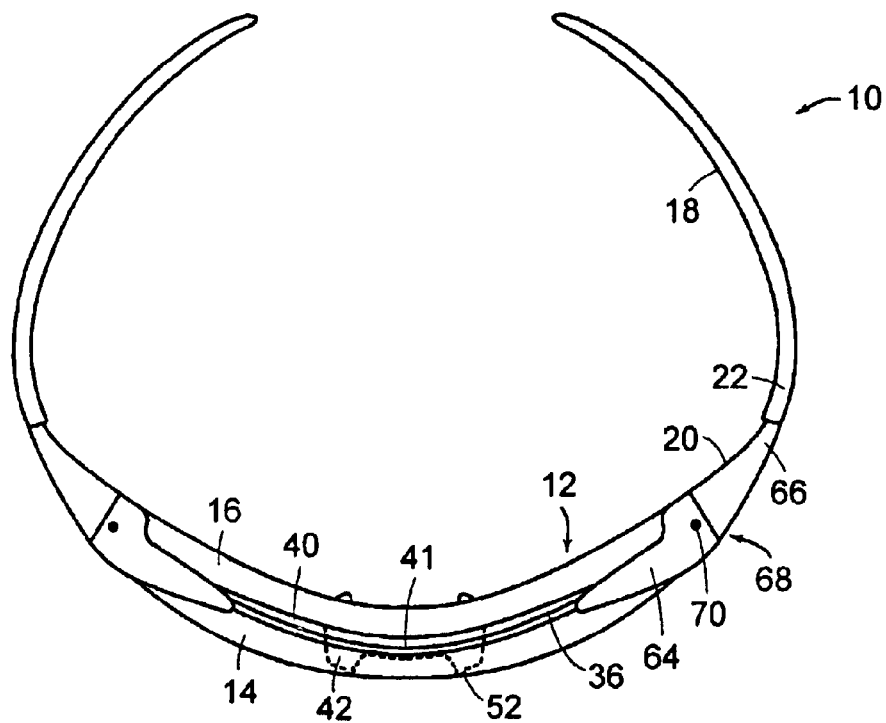
FIG. 7 is a top plan view of another alternative embodiment of the eyewear of the present invention.

In another embodiment, illustrated in FIG. 7, in which connecting members 20 may be formed of a first portion 64 and a second portion 66 pivotally connected to one another by a hinge 68. In the illustrated embodiment, hinge 68 includes a pin 70 received by apertures (not shown) formed in first portion 64 and second portion 66.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. Eyewear with a replaceable lens comprising, in combination:
   an elongate center member;
   a pair of temple arms;
   a pair of connecting members, each connecting member secured to one of the temple arms and to the center member, and having a slot formed in a surface thereof; and
   a lens received in the slots of the connecting members, a rear surface of the lens along an upper edge of the lens being spaced forwardly from the center member so as to form a gap therebetween.

2. The eyewear of claim 1, further comprising a nosepiece at a lower edge of the lens.

3. The eyewear of claim 2, wherein the nosepiece is an inverted V-shaped member.

4. The eyewear of claim 2, wherein the nosepiece is secured to a pair of notches formed in a recess formed in the lower edge of the lens.

5. The eyewear of claim 2, wherein the nosepiece includes a pair of projections, each projection engaging a notch formed in a recess in the lower edge of the lens.

6. The eyewear of claim 2, wherein the nosepiece includes a pair of frustoconical projections, each frustoconical projection engaging a notch formed in a recess in the lower edge of the lens.

7. The eyewear of claim 6, wherein each frustoconical projection includes a planar surface extending substantially perpendicular to a base of the frustoconical projection.

8. The eyewear of claim 7, wherein the planar surface is substantially flush with an edge surface of the recess of the lens.

9. The eyewear of claim 2, wherein the nosepiece includes a pair of planar surfaces and a pair of frustoconical members, each frustoconical member extending outwardly from one of the planar surfaces, having a base spaced from the one of the planar surfaces, and engaging a notch formed in a recess in the lower edge of the lens, the planar surfaces abutting against the rear surface of the lens, the planar surfaces and frustoconical members cooperating to secure the nosepiece to the lens.

10. The eyewear of claim 9, wherein each frustoconical member includes a planar surface extending substantially perpendicular to a base of the frustoconical member, the planar surface of the frustoconical member being substantially flush with an edge surface of the recess of the lens.

11. The eyewear of claim 2, further comprising a plurality of rearwardly extending fins on a rear surface of the nosepiece.

12. The eyewear of claim 1, wherein the center member is curved rearwardly.

13. The eyewear of claim 1, wherein the lens comprises a single piece lens.

14. The eyewear of claim 1, wherein the center member is formed of a rigid material.

15. The eyewear of claim 1, wherein the center member is formed of a carbon fiber composite.

16. The eyewear of claim 1, wherein each temple arm is of unitary construction with a connecting member.

17. The eyewear of claim 1, wherein each temple arm is formed of beta titanium.

18. The eyewear of claim 1, wherein each connecting member is of unitary construction with the center member.

19. The eyewear of claim 1, wherein each temple arm and each connecting member is of unitary construction with the center member.

20. The eyewear of claim 1, wherein each temple arm is pivotally secured to a connecting member by a hinge.

21. The eyewear of claim 1, wherein each connecting member includes a first portion and a second portion connected to the first portion by a hinge.

22. Eyewear with a replaceable lens comprising, in combination:

an elongate center member;

a pair of temple arms;

a pair of connecting members, each connecting member secured to one of the temple arms and to the center member and having a slot formed in a surface thereof; and a lens having an upper edge, a first tab at a first end of the upper edge, and a second tab at an opposed second end of the upper edge, the tabs being received in the slots of the connecting members such that a gap is formed between an outward surface of the center member and a rear surface of the lens along the upper edge of the lens.

23. The eyewear of claim 22, further comprising an inverted V-shaped nosepiece secured to a pair of notches formed in a recess in a lower edge of the lens.

24. The eyewear of claim 23, wherein the nosepiece includes a pair of projections, each projection engaging one of the notches.

25. The eyewear of claim 24, wherein the nosepiece includes a pair of frustoconical projections, each frustoconical projection engaging one of the notches.

26. The eyewear of claim 25, wherein each frustoconical member includes a planar surface extending substantially perpendicular to a base of the frustoconical member, the planar surface being substantially flush with an edge surface of the recess of the lens.

27. The eyewear of claim 23, wherein the nosepiece includes a pair of planar surfaces and a pair of frustoconical members, each frustoconical member extending outwardly from one of the planar surfaces, having a base spaced from the one of the planar surfaces, and engaging one of the notches, the planar surfaces abutting against the rear surface of the lens, the planar surfaces and frustoconical members cooperating to secure the nosepiece to the lens.

28. The eyewear of claim 23, further comprising a plurality of rearwardly extending fins on a rear surface of the nosepiece.

29. The eyewear of claim 22, wherein the center member is curved rearwardly.

30. The eyewear of claim 22, wherein the lens comprises a single piece lens.

31. The eyewear of claim 22, wherein the center member is formed of a rigid material.

32. The eyewear of claim 22, wherein the center member is formed of a carbon fiber composite.

33. The eyewear of claim 22, wherein each temple arm is formed of beta titanium.

34. Eyewear with a replaceable lens comprising, in combination:

an elongate center member;

a pair of temple arms;

a pair of connecting members, each connecting member secured to one of the temple arms and to the center member, and having a slot formed in a lower surface thereof;

a lens having a lower edge and an upper edge, a recess formed in the lower edge, a first tab at a first end of the upper edge, and a second tab at an opposed second end of the upper edge, the tabs being received in the slots of the connecting members such that a gap is formed between an outward surface of the center member and a rear surface of the lens along the upper edge of the lens between the connecting members; and an inverted V-shaped nosepiece is formed of a pair of arms, each arm including a projection and a planar surface, each projection engaging a notch formed in the recess and each planar surface abutting against a rear surface of the lens such that the projections and planar surfaces cooperate to secure the nosepiece to the lens.

35. Eyewear with a replaceable lens comprising, in combination:

an elongate center member;

a pair of temple arms;

a pair of connecting members, each connecting member secured to one of the temple arms and to the center member, and having a slot formed in a surface thereof; and a lens having an upper edge, a first end of the upper edge being received in the slot formed in one of the connecting members, an opposed second end of the upper edge being received in the slot formed in the other of the connecting members, the upper edge of the lens between its first and second ends being spaced from the center member so as to form a continuous gap therebetween.

36. The eyewear of claim 35, further comprising a nosepiece at a lower edge of the lens.

37. The eyewear of claim 36, wherein the nosepiece is an inverted V-shaped member.

38. The eyewear of claim 36, wherein the nosepiece is secured to a pair of notches formed in a recess formed in the lower edge of the lens.

39. The eyewear of claim 36, wherein the nosepiece includes a pair of projections, each projection engaging a notch formed in a recess in the lower edge of the lens.

40. The eyewear of claim 36, wherein the nosepiece includes a pair of frustoconical projections, each frustoconical projection engaging a notch formed in a recess in the lower edge of the lens.

41. The eyewear of claim 40, wherein each frustoconical projection includes a planar surface extending substantially perpendicular to a base of the frustoconical projection.

42. The eyewear of claim 41, wherein the planar surface is substantially flush with an edge surface of the recess of the lens.

43. The eyewear of claim 36, wherein the nosepiece includes a pair of planar surfaces and a pair of frustoconical members, each frustoconical member extending outwardly from one of the planar surfaces, having a base spaced from the one of the planar surfaces, and engaging a notch formed in a recess in the lower edge of the lens, the planar surfaces abutting against the rear surface of the lens, the planar surfaces and frustoconical members cooperating to secure the nosepiece to the lens.

44. The eyewear of claim 43, wherein each frustoconical member includes a planar surface extending substantially perpendicular to a base of the frustoconical member, the planar surface of the frustoconical member being substantially flush with an edge surface of the recess of the lens.

45. The eyewear of claim 36, further comprising a plurality of rearwardly extending fins on a rear surface of the nosepiece.

46. The eyewear of claim 35, wherein the center member is curved rearwardly.

47. The eyewear of claim 35, wherein the lens comprises a single piece lens.

48. The eyewear of claim 35, wherein the center member is formed of a rigid material.

49. The eyewear of claim 35, wherein the center member is formed of a carbon fiber composite.

50. The eyewear of claim 35, wherein each temple arm is formed of beta titanium.

51. The eyewear of claim 35, wherein each temple arm is of unitary construction with a connecting member.

52. The eyewear of claim 35, wherein each connecting member is of unitary construction with the center member.

53. The eyewear of claim 35, wherein each temple arm and each connecting member is of unitary construction with the center member.

54. The eyewear of claim 35, wherein each temple arm is pivotally secured to a connecting member by a hinge.

55. The eyewear of claim 35, wherein each connecting member includes a first portion and a second portion connected to the first portion by a hinge.

* * * * *